United States Patent [19]
Souma

[11] Patent Number: 5,172,696
[45] Date of Patent: Dec. 22, 1992

[54] PHOTOELECTRIC SPHYGMOMANOMETER OF VOLUME OSCILLOMETRIC METHOD-TYPE

[75] Inventor: Takahiro Souma, Nakai, Japan

[73] Assignee: Terumo Kabushiki Kaisha, Tokyo, Japan

[21] Appl. No.: 606,076

[22] Filed: Oct. 30, 1990

[30] Foreign Application Priority Data

Oct. 31, 1989 [JP] Japan .................. 1-281880

[51] Int. Cl.$^5$ .............................................. A61B 5/02
[52] U.S. Cl. .................................. 128/664; 128/667;
  128/672; 128/677; 128/687
[58] Field of Search ............... 128/633, 664, 665, 666,
  128/667, 672, 676, 677, 680–683, 687

[56] References Cited

U.S. PATENT DOCUMENTS

| | | | |
|---|---|---|---|
| 4,301,808 | 11/1981 | Taus | 128/689 |
| 4,524,777 | 6/1985 | Kisioka et al. | 128/677 |
| 4,621,643 | 11/1986 | New, Jr. et al. | 128/666 |
| 4,824,242 | 4/1989 | Frick et al. | 128/666 |
| 4,844,084 | 7/1989 | Yamasawa | 128/667 |
| 4,846,189 | 7/1989 | Sun | 128/667 |
| 4,862,895 | 9/1989 | Yamasawa et al. | 128/667 |
| 4,907,594 | 3/1990 | Muz | 128/633 |
| 4,944,304 | 7/1990 | Nishina | 128/667 |

FOREIGN PATENT DOCUMENTS

| | | |
|---|---|---|
| 0102816 | 3/1984 | European Pat. Off. . |
| 3723881 | 1/1989 | Fed. Rep. of Germany . |
| 62-194834 | 8/1987 | Japan . |

*Primary Examiner*—Lee S. Cohen
*Assistant Examiner*—K. M. Pfaffle
*Attorney, Agent, or Firm*—Beveridge, DeGrandi & Weilacher

[57] ABSTRACT

A photoelectric sphygmomanometer of volume oscillometric method-type is provided with regulating means for regulating quantity of light, carrier-wave gain and pulsation gain based upon the level of the carrier wave immediately after the start of cuff depressurization. This makes it possible to perform regulation after the start of depressurization and to eliminate an inability to take a measurement due to a fluctuation in the level of light received.

16 Claims, 11 Drawing Sheets

PHOTOELECTRIC SPHYGMOMANOMETER OF VOLUME OSCILLOMETRIC METHOD-TYPE

BACKGROUND OF THE INVENTION

1. Field of the Invention

This invention relates to a photoelectric sphygmomanometer of volume oscillometric method-type and, more particularly, to regulation of the quantity of light and gain of such a sphygmomanometer for a stable measurement.

2. Description of the Prior Art

In a conventional photoelectric sphygmomanometer of volume oscillometric method-type, measurement is performed after certain regulations are made. Specifically, when a cuff of the sphygmomanometer is being inflated, cuff-inflation is halted temporarily, the quantity of light is regulated and then the level of carrier wave pulsation is regulated so as to be maximized without being saturated within the dynamic range of an amplifier. The gain of pulsation following detection is also regulated so as to be maximized without being saturated within the dynamic range of a pulsation amplifier.

However, there are cases where the level of light received in such a sphygmomanometer changes owing to a variance in the transmission and absorption of light of a tissue of a living body. This variance can be ascribed to a change in the positional relationship between an artery and a light-emitting or light-receiving element, which can occur between the time of the regulation made during pressurization and the time at which blood pressure is measured at depressurization. The variance can also be ascribed to the color of the skin, etc. In such case, the carrier wave can saturate and surpass the dynamic range of the amplifier. A measurement cannot be taken until such saturation is eliminated.

SUMMARY OF THE INVENTION

An object of the present invention is provide a photoelectric sphygmomanometer of volume oscillometric method-type in which an inability to perform measurement due to a change in the level of received light is eliminated by performing a re-regulation after the start of depressurization.

In a case where the above-mentioned re-regulation is performed after the start of depressurization, the same regulation time is required if the regulation performed is the same as at the time of pressurization, as carried out conventionally. Consequently, measurement time is prolonged and congestion of blood can result.

Accordingly, another object of the invention is to provide a photoelectric sphygmomanometer of volume oscillometric method-type which greatly shortens the time needed for re-regulation.

Since the quantity of received light varies generally depending upon cuff inflation, fine regulation is required within the limited scope of the dynamic range of the amplifier. In the example of the prior art described above, however, only rough regulation is possible.

Accordingly, a further object of the invention is to provide a photoelectric sphygmomanometer of volume oscillometric method-type in which the error of regulation is minimized by finely regulating the quantity of light, thereby making stable measurement possible.

According to the present invention, the foregoing objects are attained by providing a photoelectric sphygmomanometer of volume oscillometric method-type for measuring blood pressure by detecting pulsation based on absorption and reflection of far-infrared light by blood when a inflating cuff attached to a part of the body where measurement is to be taken is gradually deflated, comprising regulating means for regulating quantity of light, carrier-wave gain and pulsation gain based on the level of the carrier wave immediately after start of depressurization.

The regulating means includes memory means for storing a relationship among light-quantity regulation steps, carrier-wave gain regulation steps and pulsation-gain regulation steps.

The regulating means is set in such a manner that variations in pulsation amplitude due to a change in the light-quantity regulation steps, carrier-wave gain regulation steps and pulsation-gain regulation steps become substantially equal.

The regulating means has sub-steps obtained by equally dividing intervals between the light-quantity regulation steps.

In the arrangement described above, the regulation of light quantity and gain is performed once in the vicinity of the mean blood pressure in the course of cuff inflation. Thereafter, re-regulation of the light-quantity and carrier-wave gain is carried out at the beginning of cuff deflation, which takes places after the pressure rise attains a set value. This enables regulation to be performed with assurance. In addition, at the time of the re-regulation, it is no longer necessary to carry out regulation again by observing the amplitude of pulsation. Furthermore, the regulation of carrier wave and pulsation gain involves a limited number of steps. Therefore, in order to finely regulate the scope of dynamic range of the carrier wave within the dynamic range of its amplifier, a fine regulation based on the quantity of light is carried out again.

According to the present invention, there can be provided a photoelectric sphygmomanometer of volume oscillometric method-type in which re-regulation is carried out after the start of cuff-deflation, thereby eliminating an inability to perform measurement due to a change in the level of received light.

Further, there can be provided a photoelectric sphygmomanometer of volume oscillometric method-type in which the time required for re-regulation can be greatly curtailed.

Further, there can be provided a photoelectric sphygmomanometer of volume oscillometric method-type in which the error of regulation is minimized by finely regulating the quantity of light, thereby making stable measurement possible.

More specifically, it is possible to regulate a change in the level of a carrier wave due to a variation in the quantity of received light, which depends upon cuff-inflation, thereby enabling reliable detection of pulsation and accurate measurement. In addition, when a re-regulation is made, it is possible to avoid prolongation of measurement time ascribable to an regulation time the same as that required by the regulation performed in the middle of cuff-inflation. This reduces the occurrence of blood congestion and alleviates discomfort. Since the regulation of the amplitude of carrier-wave is performed in a very proper accuracy, saturation can be prevented and accurate measurement can be performed.

Further objects, features and advantages of the present invention will become apparent from the following detailed description of embodiments of the present invention with reference to the accompanying drawings.

DESCRIPTION OF THE PREFERRED EMBODIMENT

In the present embodiment, quantity of light and gain are regulated.

(1) In the course of cuff inflation (in the vicinity of mean blood pressure), the cuff-inflating operation is temporarily halted, a gain regulation of carrier wave is performed by mainly regulating the level of light quantity, and then pulsation gain is regulated. Thereafter, regulation of the carrier-wave level is performed again at the immediate depressurization after the cuff is inflated to the set value.

(2) The change in final pulsation amplitude when the quantity of light can be changed by one step, when the carrier-wave gain can be changed by one step and when the pulsation gain can be changed by one step is made the same. If, as a result, carrier-wave gain is lowered by one step at the time of the above-mentioned re-regulation, the pulsation gain is raised by one step; conversely, if the quantity of light is raised by one step, pulsation gain is lowered by one step. Regulation is thus concluded to enter the measurement phase. Otherwise, regulation is performed with obtaining the relationship among the steps of light quantity and carrier-wave gain and the gain of pulsation without setting gain corresponding to each steps to be same.

As the result, a fine regulation is performed without checking pulsation level at the time of re-regulation. If measuring and checking pulsation level are performed, it becomes necessary to wait until the disorder of pulsation, which happens at the change of the pulsation gain, is stabilized. The present regulation can remove the stabilizing time, about 0.5 sec, from regulating process.

(3) It is so arranged that the amplitude of the pulsation is doubled by changing one step, sub steps are provided, which change in accordance with the magnification corresponding to the above mentioned step, e.g., a magnification of 1.25×, 1.5×, 1.75×, and regulation is so performed that the carrier-wave level falls into the dynamic range, e.g., 20%–40%, of the carrier-wave amplifier. Thereafter, fine regulation is strictly performed so as to approach 40% to the maximum possible extent.

An embodiment of the present invention will now be described in detail in accordance with the accompanying drawings.

Figure 1:
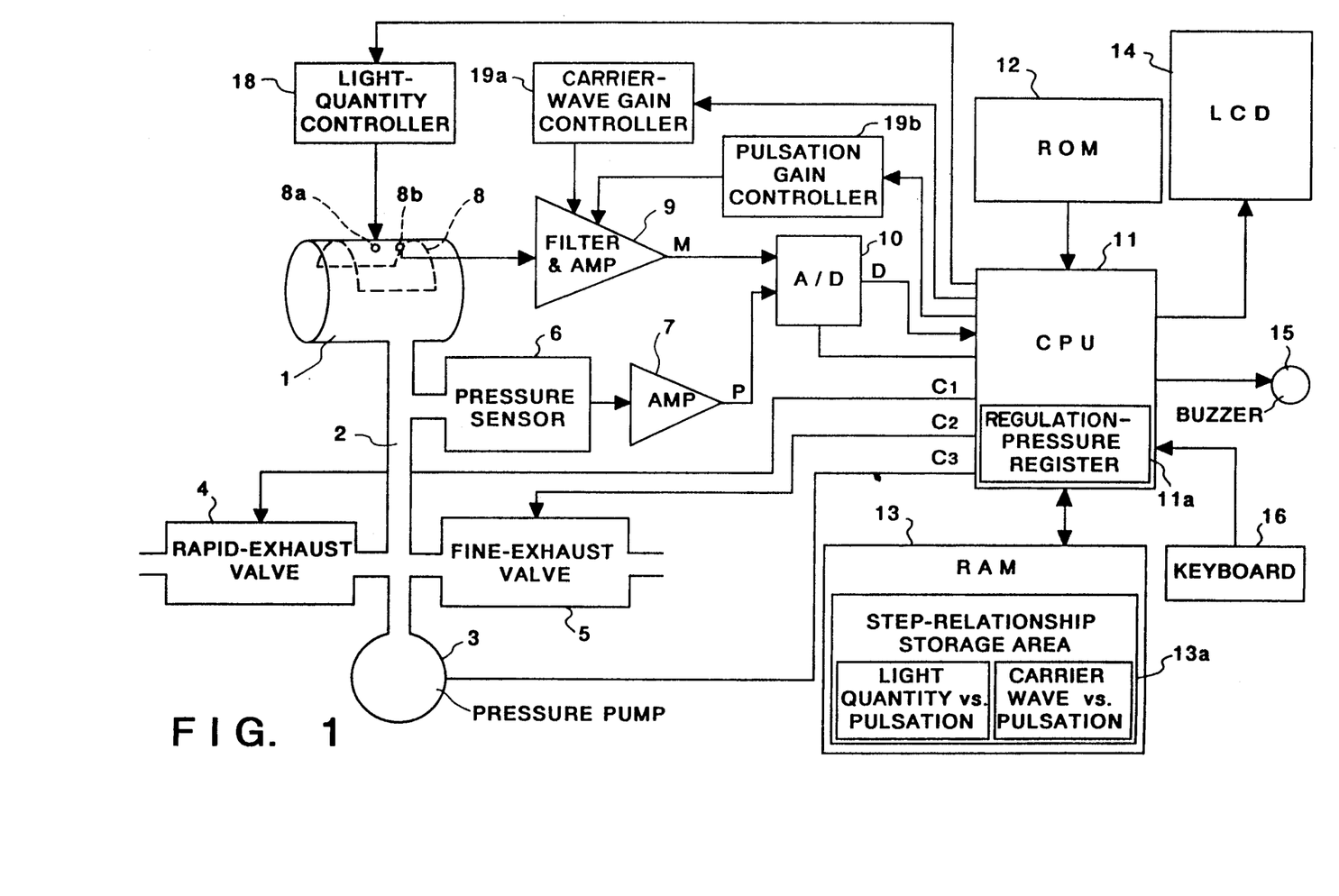
FIG. 1 is a block diagram showing the construction of an electronic sphygmomanometer embodying the present invention.

FIG. 1 is a block diagram showing the construction of a photoelectric sphygmomanometer of volume oscillometric method-type embodying the present invention. In FIG. 1, numeral 1 denotes a cuff fastened to the wrist or fingertip of a patient. Numeral 2 denotes a rubber tube forming a passageway for air to and from the cuff 1. Numeral 3 denotes a pressure pump for inflating the cuff 1. Numeral 4 designates a rapid-exhaust valve for rapidly reducing the pressure within the cuff 1. Numeral 5 represents a fine-exhaust valve for reducing the pressure within the cuff 1 at a constant rate (e.g., 2–3 mmHg/sec). A pressure sensor 6 varies an electrical parameter in dependence upon cuff pressure. A pressure detecting amplifier (AMP) 7 detects the electrical parameter of the pressure sensor 6, converts the parameter into an electric signal, amplifies the signal and outputs an analog cuff-pressure signal P.

A pulsation sensor 8 arranged inside the cuff 1 includes an LED (light-emitting diode) 8a for irradiating pulsating arterial blood with light, and a phototransistor 8b for detecting light reflected from the arterial blood. A pulsation-detecting filtering amplifier (FILTER and AMP) 9 amplifies the output signal of phototransistor 8b and delivers an analog pulsation signal M (a signal indicative of a volumetric change within a blood vessel). A light-quantity controller 18 which varies the quantity of light automatically is connected to the LED 8a. Connected to the pulsation-detecting filtering amplifier 9 are a carrier-wave gain controller 19a which varies carrier-wave gain automatically, and a pulsation-gain controller 19b which varies pulsation gain automatically. Numeral 10 denotes an A/D converter (A/D) for converting the analog signals M and P into digital data D.

Numeral 11 is a control unit (CPU) for principal control of the photoelectric sphygmomanometer of this embodiment. The CPU 11 has a regulation-pressure register 11a for storing a set value of the pressure at the time of cuff inflation. The details of control will be described later in accordance with the flowcharts of FIGS. 6A, 6B, 7A and 7B. Numeral 12 represents a ROM for storing control programs, of the kind shown in FIGS. 6A, 6B, 7A and 7B, for example, run by the CPU 11. A RAM 13 is equipped with a data memory, image memory, etc. The RAM 13 has a step-relationship storage area 13a for storing the relationship among the regulation steps of light quantity, the regulation steps of carrier-wave gain, and the regulation steps of pulsation gain. A liquid-crystal display (LCD) 14 displays the data stored in the image memory. A keyboard 16 is operated by the user to command the start of measurement, set a regulation pressure value, etc. A buzzer 15 is for informing the user of the fact that a key on the keyboard 16 has been pressed, of the fact that measurement has ended, etc. In this embodiment, the CPU 11 is provided with the regulation-pressure register 11a. Alternatively, however, the RAM 13 can be provided with a regulation-pressure storage area.

Figure 2:
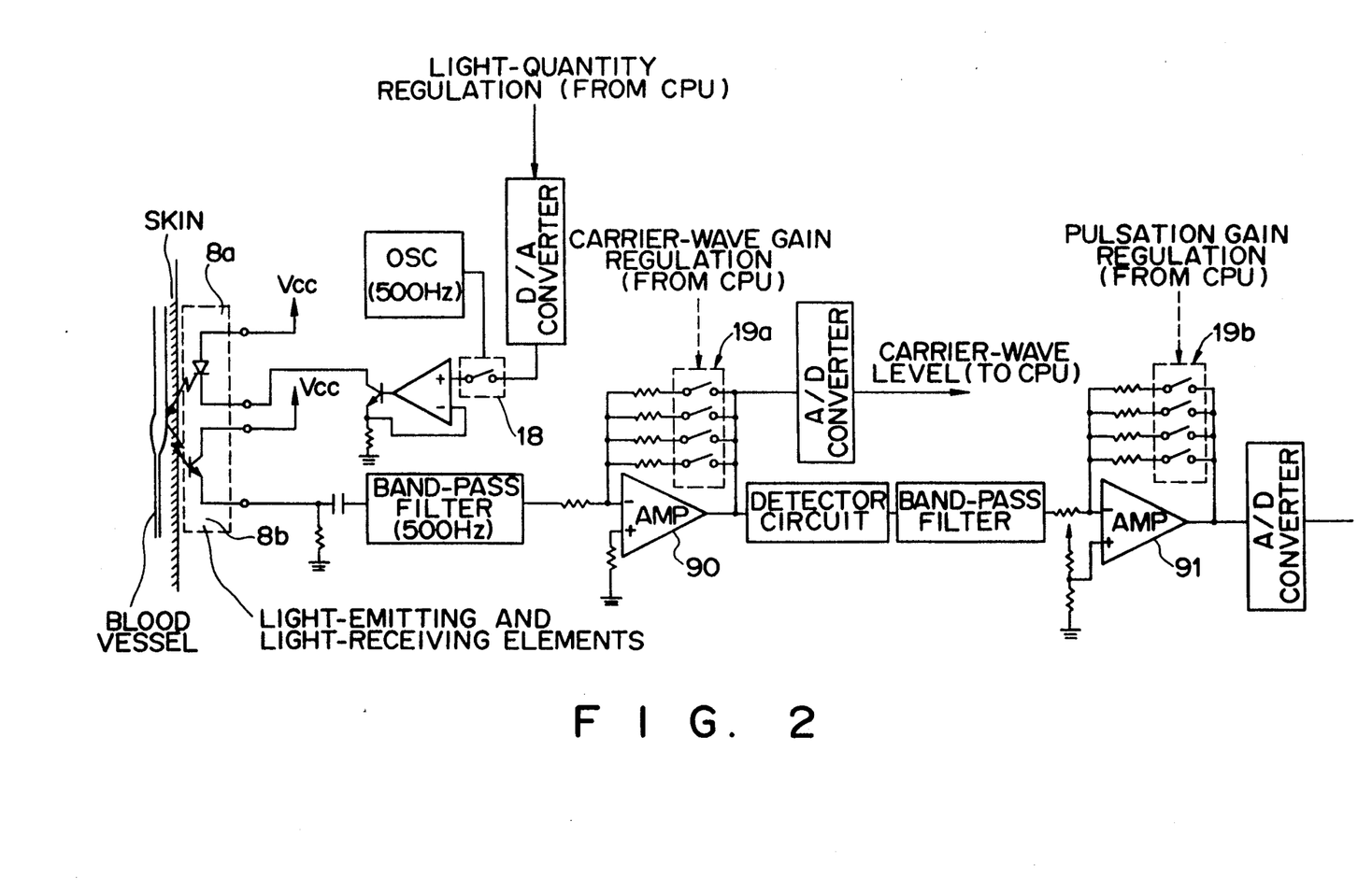
FIG. 2 is a circuit diagram showing the details of a pulsation detector in the electronic sphygmomanometer of the embodiment.

FIG. 2 is a detailed circuit diagram of the pulsation sensor section, which includes the pulsation sensor 8, filtering amplifier 9, light-quantity controller 18, carrier-wave gain controller 19a and pulsation gain controller 19b of FIG. 1. The circuits which perform the functions of the blocks shown in FIG. 1 are indicated by the same reference numbers.

Figure 3:
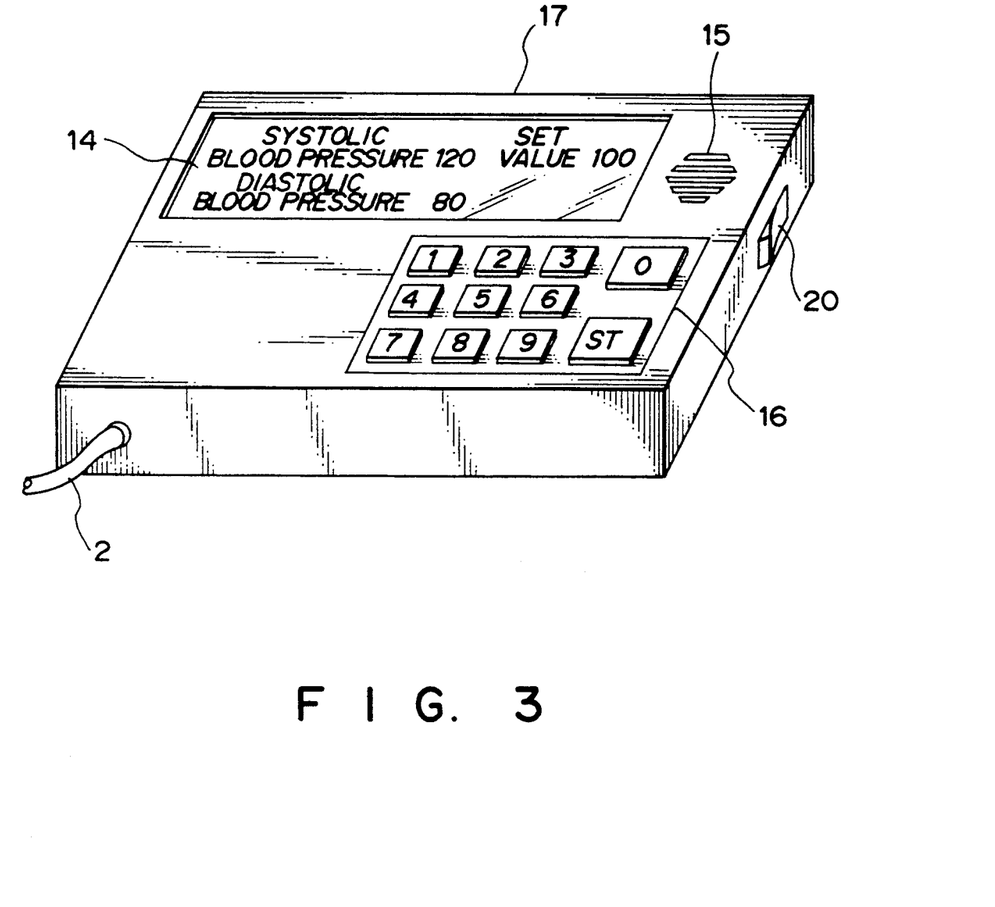
FIG. 3 is a perspective view showing the external appearance of the electronic sphygmomanometer of the embodiment.

FIG. 3 is a perspective view showing the exterior of the photoelectric sphygmomanometer of this embodiment. In FIG. 3, numeral 17 denotes the main body of the sphygmomanometer which contains the foregoing components with the exception of the cuff 1 and pulsation sensor 8. The rubber tube 2, which is connected to the cuff 1 and pulsation sensor 8, neither of which is shown in FIG. 3, includes a signal line (not shown) connected to the pulsation sensor 8. The LCD display panel 14 employs a comparatively large, dot matrix-type display panel and therefore is capable of displaying a variety of dot-pattern information (e.g., characters, graphics, signal waveforms, etc.). Numeral 20 denotes a power-supply switch. The keyboard 16 has a measurement-start switch (ST) and numeric keys for setting an regulation pressure value.

Figure 4A:
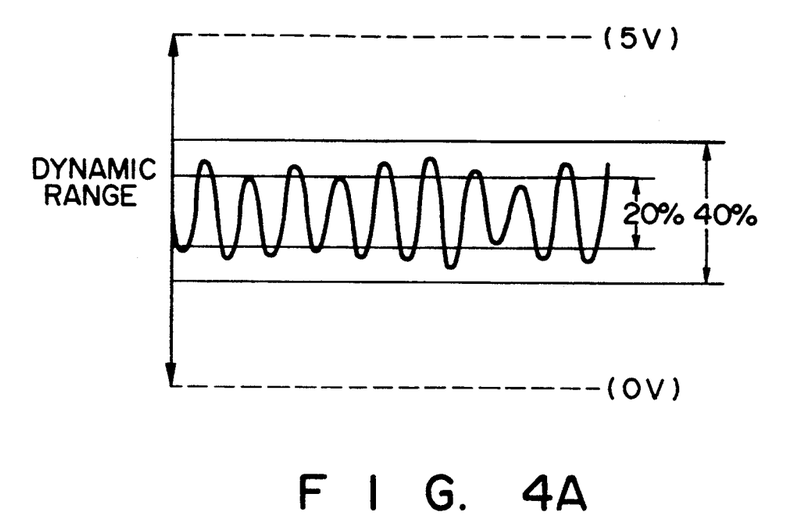
FIGS. 4A and 4B are diagrams showing examples of output waveforms associated with various portions shown in FIG. 2.
Figure 4B:
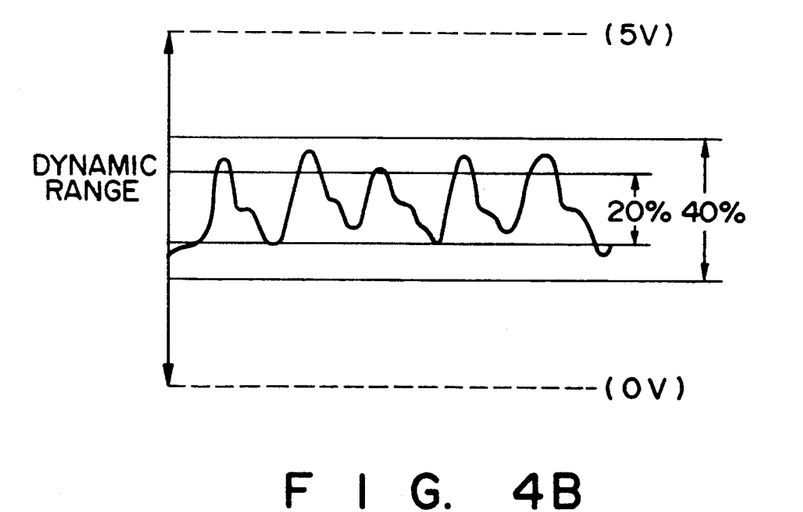

FIGS. 4A and 4B are diagrams showing examples of outputs from the amplifiers of carrier-wave level and pulsation output. In this embodiment, carrier-wave level is regulated to a stipulated range of 20–40% and pulsation level to a stipulated range of 20–40% at a dynamic range of 0 to 5 V.

Figure 5:
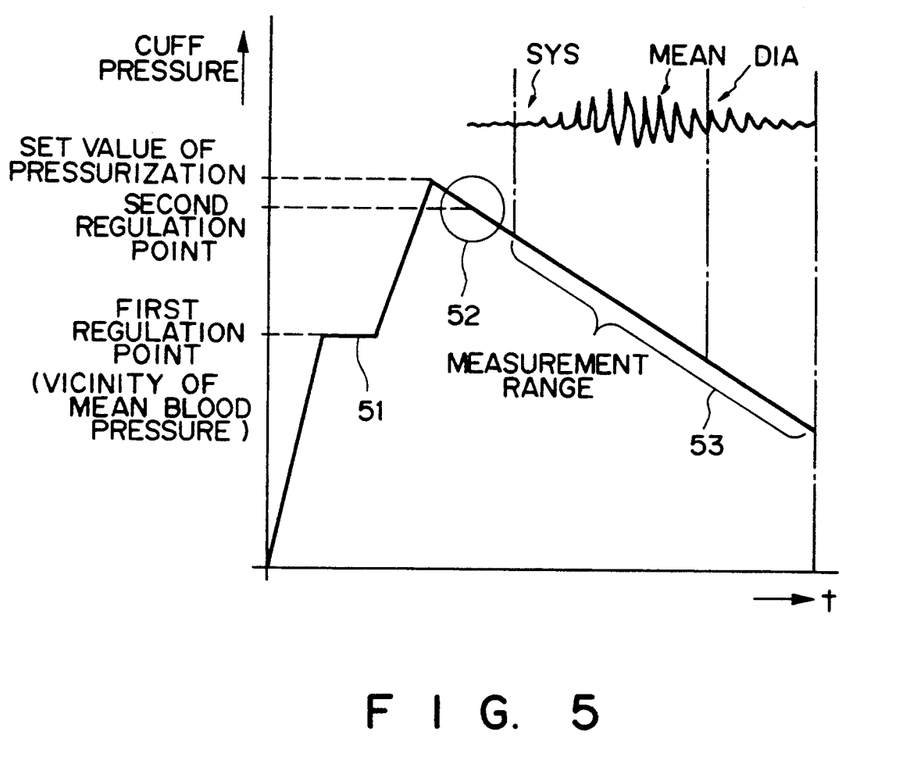
FIG. 5 is a diagram schematically showing the procedure of a measurement performed by the electronic sphygmomanometer of the embodiment.

FIG. 5 is a diagram in which the measurement procedure of the electronic sphygmomanometer of this embodiment is schematically represented by elapsed time and cuff pressure. After the start of measurement, the cuff is pressurized rapidly up to a first regulation point 51 set in the vicinity of mean blood pressure. Here a first level regulation is carried out. At the end of this regulation, the cuff is pressurized to a set inflation value higher than systolic blood pressure by an ordinary pressurizing operation, after which deflation at a constant rate is started. After the start of deflation, a level regulation is performed again at a second regulation point 52. Since it is desired that the regulation this time be carried out in as short a time as possible, the relationship among each of the regulation steps is obtained at the time of the first regulation, and regulation is performed automatically with this relationship at the second regulation. After performing the regulation of pulsation level, detection of pulsation is started subsequently and each value of blood pressure is measured.

Figure 6A:
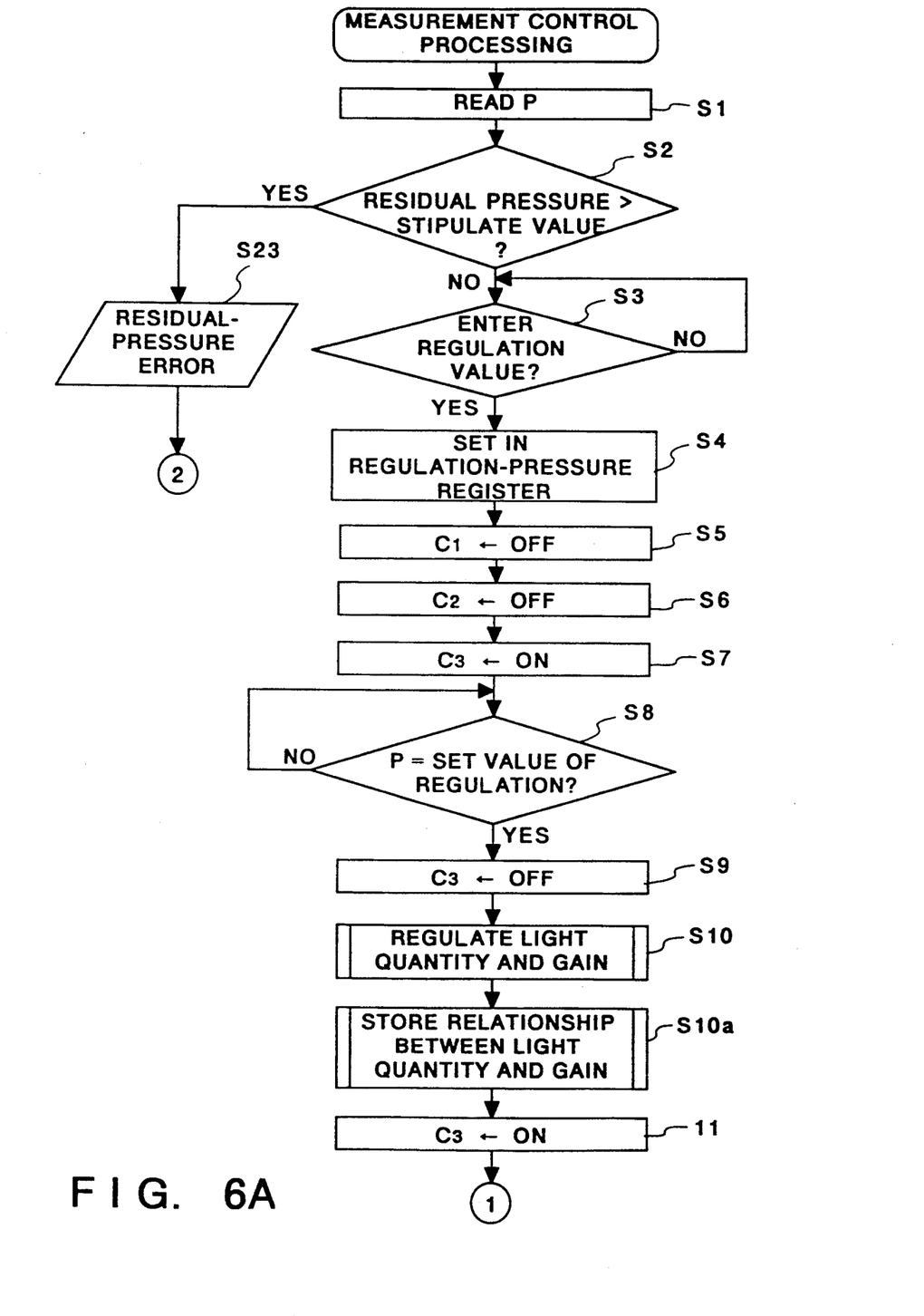
FIGS. 6A and 6B are flowcharts showing the procedure of measurement performed by the electronic sphygmomanometer of the embodiment.
Figure 6B:
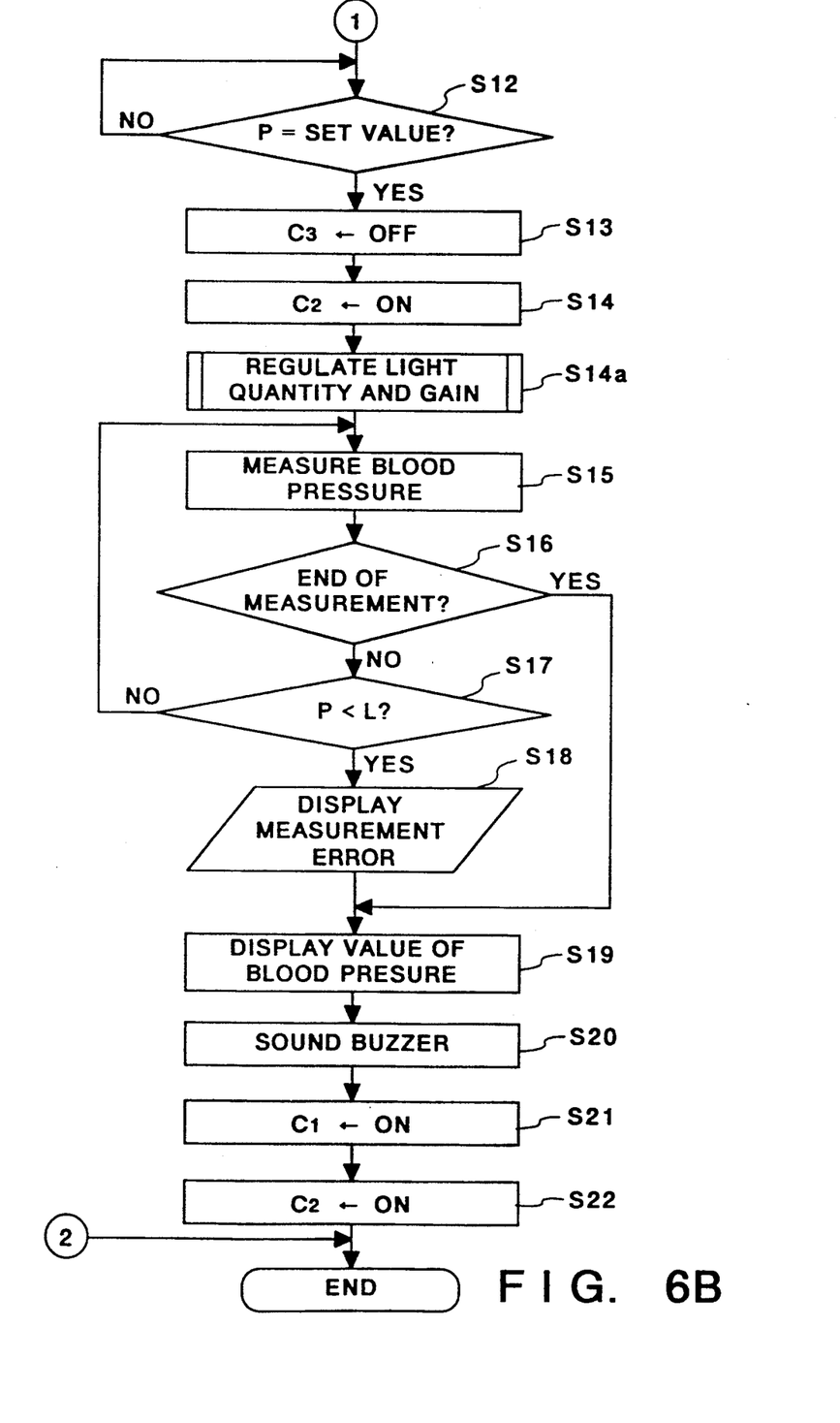

FIGS. 6A and 6B are flowchart of the stipulated processing procedure of the photoelectric sphygmomanometer of volume oscillometric method-type of this embodiment. When power is introduced to the apparatus by closing the power-supply switch 20, first the apparatus is initialized by self-diagnostic processing (not shown). When the measurement-start switch ST is subsequently pressed, processing is interrupted.

Cuff pressure P is read at step S1 and it is determined at step S2 whether residual pressure in the cuff 1 is less than a stipulated value. If the residual pressure exceeds the stipulated value, "RESIDUAL-PRESSURE ERROR" is displayed on the LCD 14. If the residual pressure is less than the stipulated value, "ENTER REGULATION-PRESSURE VALUE" is displayed and the apparatus waits for an input of the regulation-pressure value at step S3. When the regulation-pressure value is entered, this pressure value is stored in the regulation-pressure register 11a at step S4, and the rapid-exhaust valve 4 and fine-exhaust valve 5 are closed at steps S5, S6. The pressure pump 3 starts to be driven at step S7, and the apparatus waits for the cuff pressure to attain a set regulation value at step S8. As for the entry of regulation pressure, an arrangement can be adopted in which anticipated systolic blood pressure or mean blood pressure is entered, and the set value at steps from step S12 onward also are entered based on this input. When cuff pressure attains the set value, the pressure pump 3 is stopped at step S9. Next, at step S10, the quantity of light, the carrier-wave gain and the pulsation gain are regulated. This is followed by step S10a, which is processing to obtain the number of step(s) of pulsation gain with respect to a change of one step of the quantity of light or carrier-wave gain, and to store this in the step-relationship storage area 13a.

When storage of the relationship between light quantity and gain regulation ends, inflation is started again at step 11. It is determined at step S12 whether the pressure value P has attained the set value (e.g., a value within 120–210 mmHg and greater than a systolic-pressure). When the set value is obtained, operation of the pressure pump 3 is halted at step S13. The fine-exhaust discharge valve 5 is opened at step S14. When constant-rate deflation starts, the program proceeds to step S14a, at which regulation of light quantity and carrier-wave gain is performed again at step S14a based on the carrier-wave level, and regulation of pulsation gain is carried out based on the relationship obtained at step 10a, that is in conformity with the number of regulation step(s).

The measurement process begins after regulation at the second point. Cuff deflates further at the constant rate (e.g., 2–3 mmHg/sec). Meanwhile, data processing according to each function block is executed, and mean, systolic and diastolic blood pressures are measured. It is determined at step S16 whether measurement has ended. If measurement has not ended, the measurement operation proceeds and it is determined at step S17 whether the cuff pressure is lower than a predetermined value L e.g., 30 mmHg). If P<L does not hold, this means that the cuff pressure is still in the normal measurement region and the flow returns to step S15. When P<L holds, this means that the cuff pressure has a value lower than one in the normal measurement range, and therefore "MEASUREMENT ERROR" is displayed on the LCD 14. If necessary, detailed information such as the message "PRESSURIZATION INADEQUATE" can also be displayed at step S18.

If the decision rendered at step S16 is that measurement has ended, this means that the measurement process has ended in the normal measurement range. Then, at step S19, the measured values of systolic blood pressure, mean blood pressure and diastolic blood pressure are displayed on the LCD 14 and a tone signal is delivered to the buzzer 15. Preferably, the tone delivered at the end of measurement of normal blood pressures differs from that delivered at the end of measurement of abnormal blood pressures. Residual pressure in the cuff 1 is rapidly discharged and the start of next measurement is awaited at steps S21, S22.

Figure 7A:
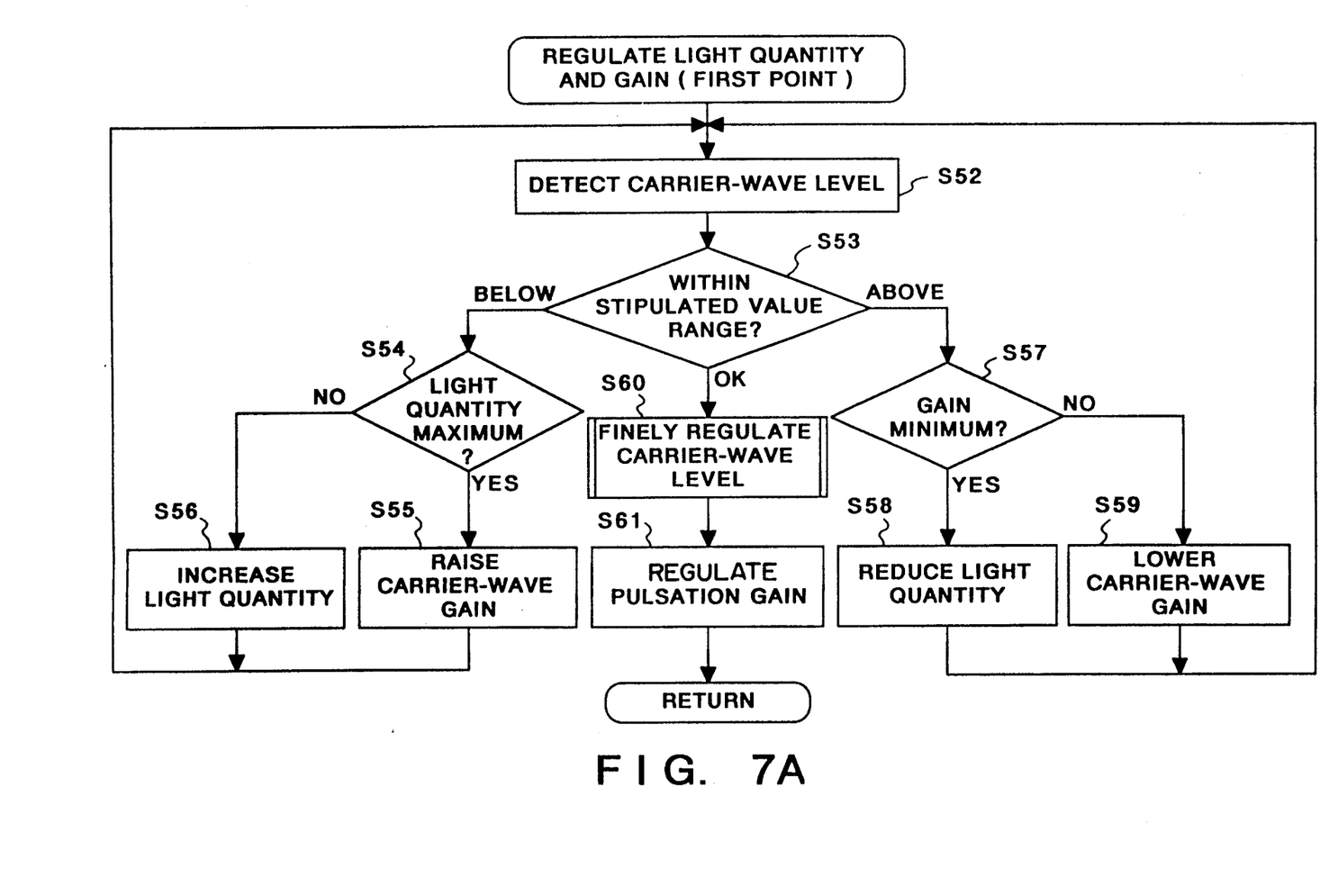
FIG. 7A is a flowchart showing the details of a step S10 in FIG. 6A.

A detailed flowchart of the light quantity and gain regulation of step S10 in FIG. 6 is shown in FIG. 7A.

Carrier-wave level is detected at step S52, and it is determined at step S53 whether the carrier-wave level lies between stipulated values (20–40% of the full scale of A/D converter 10). If the carrier-wave level is less than the range of stipulated values, then the program proceeds to step S54, at which it is determined whether the quantity of light is maximum. If it is not maximum, the D/A converter is controlled at step S56 to raise the quantity of light. If the quantity of light is maximum, then feedback gain of an amplifier 90 is controlled at step S55 to raise the gain. Following the processing of step S55 or step S56, the program returns to step S52 and the check of pulsation is repeated.

If it is found at step S53 that the carrier-wave level is greater than the stipulated value, it is determined at step S57 whether the gain is minimum. If it is not minimum, then the feedback of the amplifier 90 is controlled by the carrier-wave gain controller 19a at step S59 to lower the gain. If the carrier-wave level is minimum, the quantity of light is reduced at step S58. When the processing of step S58 or S59 ends, the program returns to step S52 and the check of carrier-wave level is repeated.

If the carrier-wave level is found to be within the range of stipulated values at step S53, fine regulation is performed at step S60 in such a manner that the carrier-wave level due to the quantity of light will becomes as close as possible to 40% of full scale of A/D converter 10. The pulsation gain is regulated by an amplifier 91 at step S61, and then the program returns.

Figure 7B:
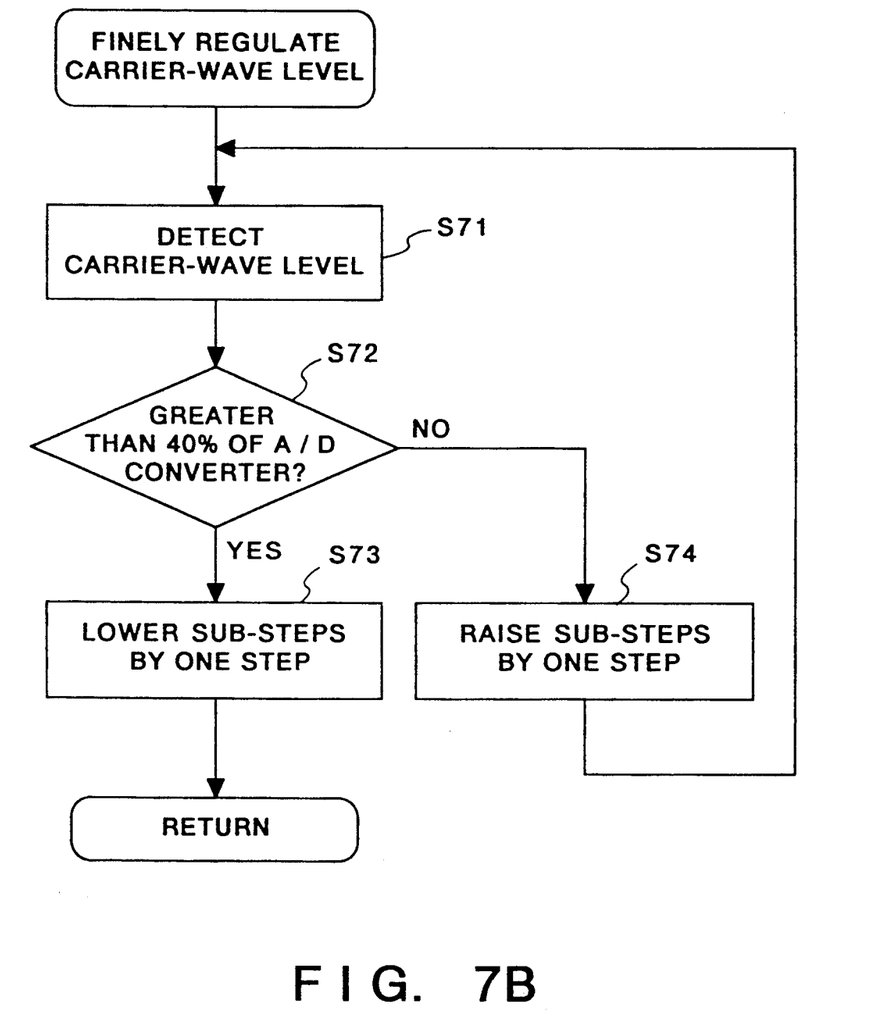
FIG. 7B is a flowchart showing the details of a step S60 in FIG. 7A.

A flowchart showing the detailed procedure of fine regulation of the carrier-wave level of step S60 is illustrated in FIG. 7B.

The carrier-wave level is detected at step S71, after which it is determined at step S72 whether the detected level is greater than 40% of the full scale of the A/D converter. If the detected level is greater than 40%, the program proceeds to step S73, at which the sub-steps are reduced by one step. If the detected level is not 40%, the program proceeds to step S74, where the sub-steps are raised by one step. The steps S71, S72, S74 are repeated in this order until the detected level exceeds 40%.

Examples of the main steps and sub-steps used in this embodiment are shown in Table 1 below.

TABLE 1

| STEP NO. | MAIN STEPS | SUB-STEPS (MAXIMUM LIGHT QUANTITY = 256) | | |
|---|---|---|---|---|
| | | ×1.25 | ×1.5 | ×1.75 |
| 1 | 4 | 5 | 6 | 7 |
| 2 | 8 | 10 | 12 | 14 |
| 3 | 16 | 20 | 24 | 28 |
| 4 | 32 | 40 | 48 | 58 |
| 5 | 64 | 80 | 96 | 112 |
| 6 | 128 | 160 | 192 | 224 |
| 7 | 256 | — | — | — |

Figure 8:
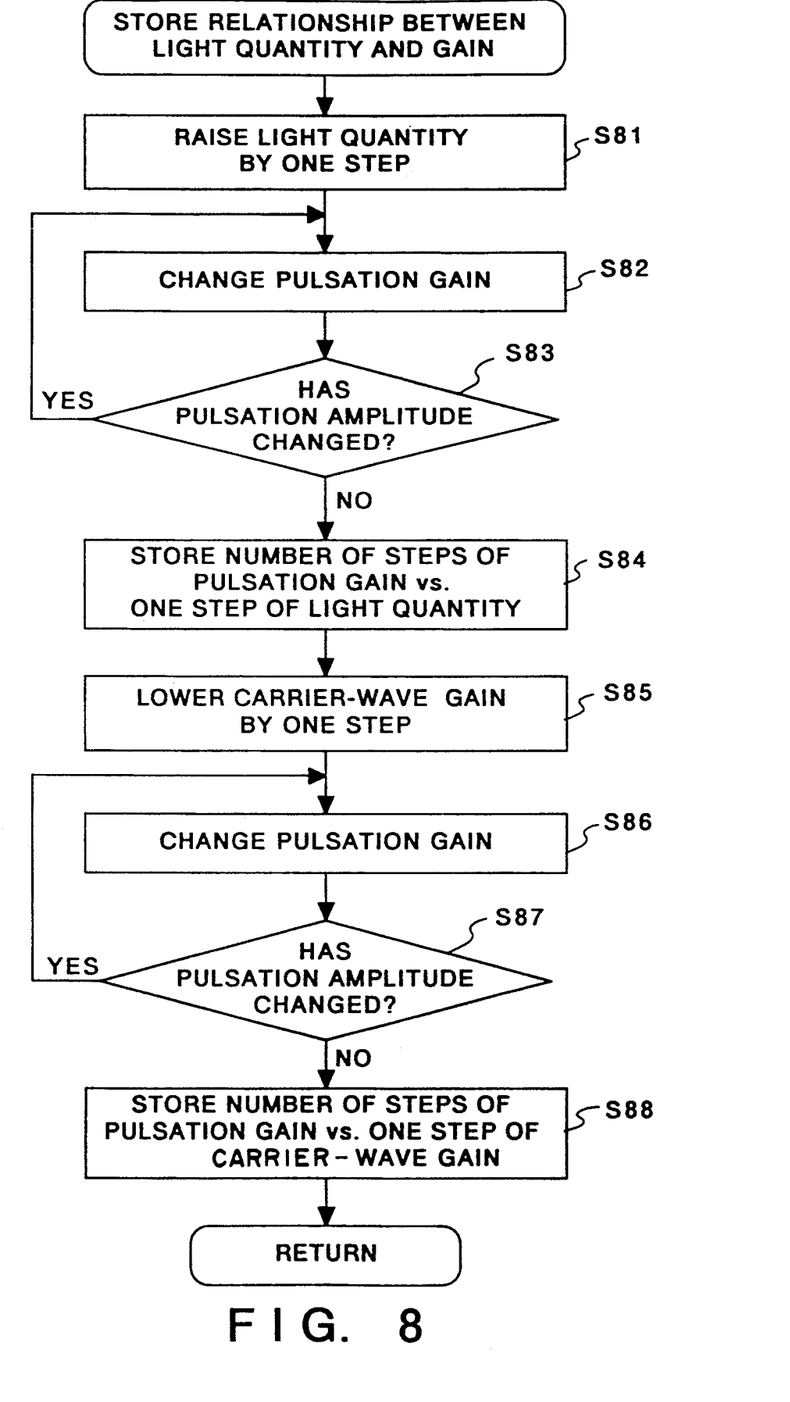
FIG. 8 is a flowchart showing the details of a step S10a in FIG. 6A.

FIG. 8 is a detailed flowchart illustrating the processing of step S10a in FIG. 6A for obtaining the relationship among the steps of light quantity and carrier-wave gain and the gain of pulsation.

First, the quantity of light is raised by one step at step S81. Then, while changing the pulsation gain step at step S82, the number of steps over which the pulsation level does not change is obtained at step S83. For example, changing the pulsation gain step at step S81 is reducing. This number is stored at step S84 and the quantity of light and pulsation gain are returned to their original values. Next, at steps S85 through S88, the carrier-wave gain is lowered by one step and the number of steps of pulsation-level change is stored in the same manner.

Figure 9:
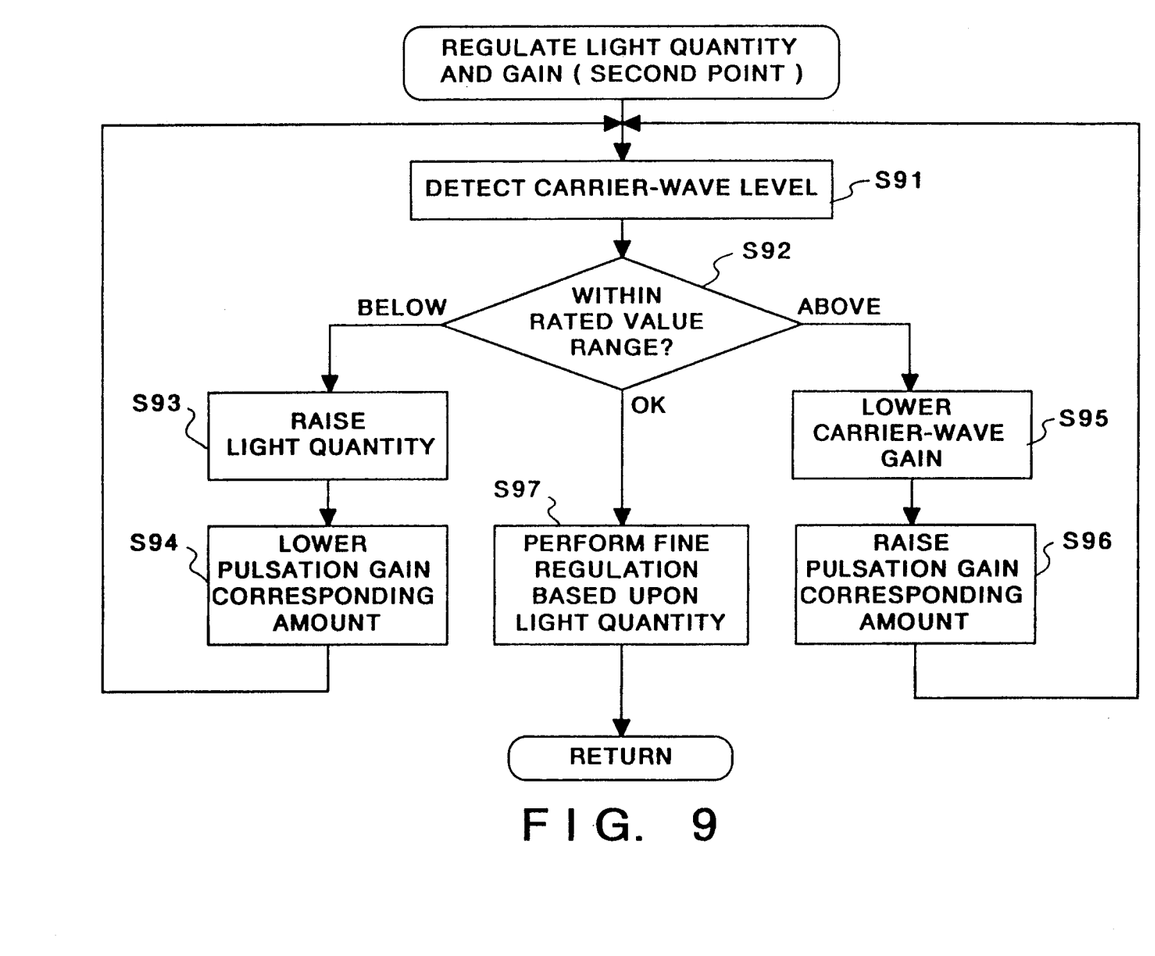
FIG. 9 is a flowchart showing the details of a step S14a in FIG. 6B.

FIG. 9 is a flowchart showing the details of the second regulation of step 14a in FIG. 6B.

First, the carrier-wave level is detected at step S91, after which it is determined whether the level lies within stipulated limits at step S92 in the same manner as at step S53 of FIG. 7A. If the level is less than the stipulated values, the quantity of light is raised by one step at step S93 and the pulsation gain is lowered at step S94 in accordance with the relationship obtained at step S10a. This is repeated until the level falls within the stipulated range. If the range is exceeded, similar processing is executed at step S95 and S96. If the level is within the stipulated range, fine regulation based on light quantity is performed at step S97 in the same manner as at step S60 in FIG. 7A, and the program returns.

Measurement of blood pressure at step S15 will now be described in brief. Specifically, cuff pressure corresponding to the point of which the pulsation signal appears is taken as systolic blood pressure, cuff pressure corresponding to the point of which amplitude of the pulsation signal is maximized is taken as mean blood pressure, and cuff pressure corresponding to the point of which the change in the size of the pulsation signal vanishes is taken as diastolic blood pressure. Alternatively, is it permissible to compute diastolic blood pressure based upon mean blood pressure, systolic blood pressure and a waveform constant obtained from pulsation of the mean blood-pressure point.

In the present embodiment, the relationship among light quantity, the steps of carrier-wave gain and the steps of pulsation is obtained. However, the objects of the invention can be attained also by designing it so that the quantity of light, one step of the carrier-wave gain and one step of the pulsation gain are in 1:1 correspondence when the circuit shown in FIG. 2 is fabricated.

Though an example in which light reflected from a blood vessel is detected is illustrated in the foregoing embodiment, an arrangement can be adopted in which light transmitted through the blood vessel is detected. In a photoelectric sphygmomanometer of volume oscillometric method-type provided with a plurality of light-receiving elements, circuitry of the kind shown in FIG. 2 is provided for each of these light-receiving elements.

As many apparently widely different embodiments of the present invention can be made without departing from the spirit and scope thereof, it is to be understood that the invention is not limited to the specific embodiments thereof except as defined in the appended claims.

What is claimed is:

1. A photoelectric volume oscillometric sphygmomanometer for measuring blood pressure based on an oscillating pulse which is detected and corresponds to an absorption of reflection of far-infrared light by blood, comprising:

a cuff for being pressurized and depressurized after being pressurized to a predetermined pressure;

means for providing far-infrared light;

means for regulating a quantity of far-infrared light provided by said means for providing far-infrared light;

means for detecting said far-infrared light reflected by blood, transmitted by blood or absorbed by blood, said means for detecting including a means for providing an oscillation pulse, said means for detecting further including a carrier-wave amplifier and an oscillating pulse amplifier;

means for regulating a gain of said carrier-wave amplifier;

means for regulating a gain of said oscillating pulse amplifier; and means for controlling said means for regulating the quantity of far-infrared light, said means for regulating the gain of said carrier-wave amplifier, and said means for regulating the gain of said oscillating pulse amplifier, such that the means for regulating the quantity of far-infrared light, the means for regulating the gain of the carrier-wave amplifier, and the means for regulating the gain of the oscillating pulse amplifier are controlled during depressurization of said cuff, without stopping the depressurization, after a beginning of depressurization of said cuff.

2. The sphygmomanometer according to claim 1, wherein said means for controlling includes a memory means for storing a relationship between a change in the carrier-wave amplifier gain and a change in the oscillating pulse amplifier gain.

3. The sphygmomanometer according to claim 2, wherein said memory means stores the relationship in such a manner that a change in an oscillating pulse amplitude based on a step change in the far-infrared light quantity is stored, and a change in the carrier-wave amplifier gain based on a change in the oscillating pulse amplifier gain is stored.

4. The sphygmomanometer according to claim 2, wherein said memory means further includes means for storing a value of said far-infrared light quantity which is equally divided into step values thereof.

5. The sphygmomanometer according to claim 1, further comprising a rubber tube and a pressure pump, wherein said rubber tube connects said cuff to said pressure pump.

6. The sphygmomanometer according to claim 5, further comprising a rapid exhaust valve connected between said pressure pump and said cuff.

7. The sphygmomanometer according to claim 6, further comprising a fine exhaust valve connected between said pressure pump and said cuff.

8. The sphygmomanometer according to claim 1, further comprising a pressure pump and a fine exhaust valve connected between said pressure pump and said cuff.

9. The sphygmomanometer according to claim 1, further comprising a keyboard connected to said means for controlling.

10. The sphygmomanometer according to claim 9, further comprising a liquid crystal display connected to said means for controlling.

11. The sphygmomanometer according to claim 10, further comprising a buzzer connected to said means for controlling.

12. The sphygmomanometer according to claim 1, further comprising a liquid crystal display connected to said means for controlling.

13. The sphygmomanometer according to claim 1, further comprising a buzzer connected to said means for controlling.

14. A method for measuring blood pressure, comprising:
connecting a sphygmomanometer cuff to a part of a body for measuring blood pressure;
setting a regulating pressure valve in a regulation pressure register;
inflating the cuff to the regulating pressure value;
illuminating a blood containing vessel in the body with far-infrared light;
measuring a relationship between a carrier-wave amplifier gain and a pulsation amplifier gain as a function of a quantity of said far-infrared light reflected from the blood, transmitted by the blood or absorbed by the blood;
storing said relationship in a memory;
resume inflating said cuff until the pressure reaches a set pressure value greater then said regulating pressure value;
after reaching the set pressure value, discontinue inflating said cuff;
slowing releasing the set pressure from the cuff;
before measuring the blood pressure, while the pressure is being released, regulating the light quantity, the carrier-wave amplifier gain and the pulsation amplifier gain based on the stored relationship;
thereafter locating a systolic value based on a pressure corresponding to a point when a pulsation signal appears;
locating a diastolic value based on a pressure corresponding to a point when the pulsation signal disappears; and
indicating said systolic and diastolic values.

15. The sphygmomanometer according to claim 14, further comprising locating a mean blood pressure value at a pressure corresponding to a point of maximum amplitude of the pulsation signal.

16. A method according to claim 14, wherein said indicating includes displaying said systolic and diastolic values on a liquid crystal display.

* * * * *

UNITED STATES PATENT AND TRADEMARK OFFICE
CERTIFICATE OF CORRECTION

PATENT NO. : 5,172,696

DATED : December 22, 1992

INVENTOR(S) : T. Souma

Page 1 of 2

It is certified that error appears in the above-identified patent and that said Letters Patent is hereby corrected as shown below:

In column 1, line 18, after "regulated", insert a comma --,--;

In column 2, line 3, change "a" (first occurrence) to --an--;

In column 2, line 59, change "an" to --a--;

In column 2, line 63, after "of" (second occurrence), insert --the--;

In column 3, line 56, after "setting", insert --the--;

In column 3, line 57, change "steps to be" to --of the steps to be the--;

In column 3, line 64, after "from", insert --the--;

In column 5, line 22, change "an" to --a--;

In column 5, line 50, after "are", insert --a--;

In column 6, line 59, after "discharged", insert a comma --,--;

In column 7, line 21, change "becomes" to --become--;

In column 7, line 22, change "full scale of" to --the full scale of the--;

In column 7, line 61, after "S84", insert a comma --,--;

In column 8, line 6, after "S93", insert a comma --,--;

In column 8, line 15, change "in brief" to --briefly--;

UNITED STATES PATENT AND TRADEMARK OFFICE
CERTIFICATE OF CORRECTION

PATENT NO. : 5,172,696

DATED : December 22, 1992

INVENTOR(S) : T. Souma

It is certified that error appears in the above-identified patent and that said Letters Patent is hereby corrected as shown below:

In claim 1, column 8, line 51, change "of" (first occurrence) to --or--;

In claim 14, column 10, line 14, change "valve" to --value--;

In claim 14, column 10, line 26, change "then" to --than--;

In claim 14, column 10, line 30, delete "set";

In claim 15, column 10, line 42, change "sphygmomanometer" to --method--; and

In claim 16, column 10, line 46, change "A" to --The--

Signed and Sealed this

Sixteenth Day of November, 1993

Attest:

BRUCE LEHMAN

*Attesting Officer*  *Commissioner of Patents and Trademarks*